(12) United States Patent
Haraguchi et al.

(10) Patent No.: US 7,180,596 B2
(45) Date of Patent: Feb. 20, 2007

(54) GAS CONCENTRATION DETECTOR

(75) Inventors: Hiroshi Haraguchi, Kariya (JP);
Tomoo Kawase, Ama-gun (JP);
Daisuke Kojima, Nagoya (JP)

(73) Assignee: Denso Corporation, Kariya (JP)

( * ) Notice: Subject to any disclaimer, the term of this patent is extended or adjusted under 35 U.S.C. 154(b) by 593 days.

(21) Appl. No.: 10/660,628

(22) Filed: Sep. 12, 2003

(65) Prior Publication Data

US 2004/0050695 A1     Mar. 18, 2004

(30) Foreign Application Priority Data

Sep. 13, 2002   (JP)   .............................. 2002-268044

(51) Int. Cl.
*G01N 21/61* (2006.01)
(52) U.S. Cl. ..................................... 356/437
(58) Field of Classification Search ..................... None
See application file for complete search history.

(56) References Cited

U.S. PATENT DOCUMENTS 6,454,931 B2 * 9/2002 Patrick et al. .............. 205/781
6,467,954 B2 * 10/2002 Honda et al. ................ 374/183
7,025,870 B2 * 4/2006 Makihara et al. ........ 205/785.5

FOREIGN PATENT DOCUMENTS

JP          9-288086          11/1997

* cited by examiner

*Primary Examiner*—Tu T. Nguyen
(74) *Attorney, Agent, or Firm*—Nixon & Vanderhye P.C.

(57) ABSTRACT

A gas concentration detector prevents deviation in output due to a difference in oxygen reactivity between electrode materials to accurately detect a specific gas component in a gas to be measured, such as NOx in an exhaust gas. A sensor element in an NOx sensor has a pump cell in a first chamber and a sensor cell for decomposing NOx and any remaining oxygen and a monitor cell for decomposing only remaining oxygen in a second chamber. An NOx concentration is detected based on a difference in current output between the sensor cell and the monitor cell. Since the sensor cell and the monitor cell have different oxygen reactivities, an output of the monitor cell is smoothed through a band-pass filter or the like so that output responses of the sensor cell and the monitor cell are made to substantially match each other, thereby eliminating any deviation in output.

17 Claims, 8 Drawing Sheets

WITHOUT SMOOTHING

WITH SMOOTHING

# GAS CONCENTRATION DETECTOR

CROSS REFERENCE TO RELATED APPLICATION

This application is based upon, claims the benefit of priority of, and incorporates by reference, the contents of Japanese Patent Application No. 2002-268044 filed Sep. 13, 2002.

BACKGROUND OF THE INVENTION

1. Field of the Invention

The present invention relates to a gas concentration detector for detecting a specific gas component in a gas to be measured by using a plurality of cells provided for in a solid electrolyte body. More specifically, the detector can be used for detecting an NOx concentration contained in the exhaust gas from an internal combustion engine of a vehicle.

2. Description of the Related Art

Generally, concern over the global environment is increasing. Correspondingly, the regulations on the exhaust gas from internal combustion engines for vehicles is becoming stricter year by year. In response to these regulations, more precise control of exhaust gas is expected. That is, the detection of harmful materials in the exhaust gas is expected, for example, detection of NOx concentrations, to feedback the result of detection to an EGR (Exhaust Gas Recirculation) system, a catalyst system. and the like.

As such, a gas concentration detector using a plurality of cells provided for an oxygen ion conductive solid electrolyte body to detect the concentration of NOx by taking advantage of a difference in activity to NOx reduction has been known. For example, see Japanese Patent Laid-Open Publication No. Hei 9-288086 (1997). Such a conventional gas concentration detector generally has a pump cell for exhausting and pumping oxygen into an exhaust gas introduced into a chamber, a monitor cell for generating an output in accordance with a concentration of oxygen remaining in the chamber, and a sensor cell for generating an output in accordance with the concentrations of remaining oxygen and NOx in the chamber. For example, pump cell voltage is feedback-controlled so that the oxygen concentration in the chamber, which is detected by the monitor cell, is kept constant. At the same time, an NOx concentration in the exhaust gas is detected based on a current value of a current flowing through the sensor cell.

Moreover, a space in the chamber is normally partitioned into a first chamber where the pump cell is placed and a second chamber where the sensor cell and the monitor cell are placed. These first and second chambers are connected to each other through a throttle. With this configuration, a variation in oxygen concentration in the vicinity of the sensor cell and the monitor cell can be decreased. However, a change in oxygen concentration in the first chamber due to a change in pump cell voltage is not immediately reflected in the oxygen concentration in the second chamber (monitor cell current value). Therefore, there is a possibility that the oxygen concentration in the second chamber may not be stabilized. In view of such a problem, the detection of the NOx concentration in an exhaust gas based on a difference in output between the sensor cell and the monitor cell has been proposed. According to such a detection, the detection accuracy is advantageously improved because a sensor output independent of the oxygen concentration in the second chamber can be obtained.

However, as chamber-side electrodes, the sensor cell uses a Pt—Rh electrode that is active to reduction of any NOx, whereas the monitor cell uses a Pt—Au electrode that is inactive to reduction of any NOx. Therefore, these electrode materials have different reactivities (responses) to oxygen. Such a difference in reactivity results from the fact that Rh contained in the sensor cell electrode has oxygen storage ability so that the sensor cell electrode is more likely to take up oxygen contained in the exhaust gas as compared with the monitor cell. As a result, the sensor cell has a low reactivity to a variation in oxygen concentration. Thus, for example, when the operation condition of an engine is changed to vary an oxygen concentration in the exhaust gas, or when a concentration of oxygen remaining in the second chamber is changed, a deviation is generated between an output current of the sensor cell and that of the monitor cell. As a result, a difference in output between the sensor cell and the monitor cell is varied to change the detected NOx value, adversely preventing accurate detection of NOx.

SUMMARY OF THE INVENTION

The present invention has been devised in view of the above problem, and has an object of providing a gas concentration detector capable of preventing deviation in output due to a difference in oxygen reactivity between electrode materials so as to realize accurate detection of a specific gas component in a gas to be measured, such as NOx in exhaust gas.

According to a first aspect of the present invention, a gas concentration detector has a sensor cell for detecting the concentration of a specific gas component in the gas to be measured upon its introduction into a chamber. Furthermore, there is a monitor cell for detecting the oxygen concentration in the chamber, while the sensor cell and the monitor cell have different oxygen reactivities. Finally, there is an electrical correction means for substantially matching the output of the sensor cell and the monitor cell to a variation in oxygen concentration.

If the sensor cell and the monitor cell have different oxygen reactivities, a deviation is generated in output between these cells when the oxygen concentration in the chamber is varied and the like. In the above-described structure, since the output responsibilities of the sensor cell and the monitor cell can be made to substantially match each other by the electrical correction means, no deviation is generated in output between the sensor cell and the monitor cell, thereby remarkably improving detection accuracy.

In the detector according to a second aspect of the invention, means for restraining an electrical reaction of at least one of the sensor cell and the monitor cell is provided as the electrical correction means. For example, the output of either the sensor cell or the monitor cell, which has a higher response to a variation in oxygen concentration, is smoothed through the electrical correction means, whereby the output response of the sensor cell and the monitor cell can be made to match each other.

In the detector according to a third aspect of the invention, the means for restraining the electrical reaction is a filter for passing or removing a specific frequency component in the output of any one of the sensor cell and the monitor cell. By using such a filter, the frequency response of any one of the sensor cell and the monitor cell is smoothed to eliminate any response deviations.

As the detector according to a fourth aspect of the invention, specifically, a band-pass filter is suitably used as the means for restraining the electrical reaction. In addition to the above-described hardware approach, a deviation in response between the sensor cell and the monitor cell can also be eliminated through a software approach that uses a signal processing means.

For example, in the detector according to a fifth aspect of the invention, a signal processing means for correcting an output of at least one of the sensor cell and the monitor cell based on an amplitude and a cycle of a pulsation of the output is provided as the electrical correction means.

For the output of the sensor cell or the monitor cell, the amplitude and the cycle of a pulsation are calculated. The correction is performed based on the calculated amplitude and cycle to restrain the pulsation, so that a deviation in output in response to a variation in oxygen concentration can be reduced, thereby remarkably improving detection accuracy.

In the detector according to a sixth aspect of the invention, the signal processing means variably sets a correction constant based on the amplitude and the cycle of the pulsation of the output of any one of the sensor cell and the monitor cell. When the correction constant is variably set so that, for example, the correction constant is increased as the amplitude and the cycle of the pulsation of the output are increased, the output is smoothed in accordance with the amplitude and the cycle of the pulsation. As a result, the response of the sensor cell and that of the monitor cell are made to match each other to decrease deviation in output.

In the detector according to a seventh aspect of the invention, the signal processing means performs smoothing correction on the respective outputs of the sensor cell and the monitor cell by using smoothing constants, respectively determined, based on the amplitudes and the cycles of the pulsations of the outputs of the sensor cell and the monitor cell.

Suitably, for both the sensor cell and the monitor cell, the smoothing constants are determined in accordance with the amplitudes and the cycles of pulsations of the sensor cell and the monitor cell respectively, so as to perform smoothing correction. As a result, since the amplitudes and the phases of pulsations of the outputs of the cells can be made to match each other, the deviation in output due to a difference in response can be eliminated.

The detector according to an eighth aspect of the invention further includes a pump cell for exhausting oxygen in the gas to be measured, introduced into the chamber, to the exterior or for introducing oxygen from the exterior so as to adjust the oxygen concentration in the chamber. By the use of the above-mentioned pump cell, for example, oxygen in the gas to be measured in the chamber can be externally exhausted to control the chamber to have a predetermined low oxygen concentration. Therefore, the detection is hardly affected by a change in oxygen concentration in the gas to be measured to facilitate the detection of the specific gas component in the gas to be measured.

In the detector according to a ninth aspect of the invention, the pump cell includes a solid electrolyte body having oxygen ion conductivity and a pair of electrodes formed on surfaces of the solid electrolyte body. The oxygen concentration in the chamber is controlled by controlling the voltage applied to the pair of electrodes in accordance with the value of the current flowing between the pair of electrodes or in accordance with the output of the monitor cell.

For example, the voltage applied to the pair of electrodes is controlled in accordance with a current value so that a current flowing between the pair of electrodes of the pump cell becomes a limiting current, whereby the chamber can be controlled to have a predetermined low oxygen concentration. Alternatively, the chamber can also be controlled to have a predetermined low oxygen concentration by controlling the voltage applied to the pair of electrodes so that an output of the monitor cell becomes a predetermined constant value.

In the detector according to a tenth aspect of the invention, the sensor cell includes a solid electrolyte body having oxygen ion conductivity and a pair of electrodes formed on surfaces of the solid electrolyte body. Furthermore, a concentration of the specific gas component and a concentration of remaining oxygen in the chamber are detected based on a current value of the current flowing between the pair of electrodes when a predetermined voltage is applied to the pair of electrodes.

When a predetermined voltage is applied to the pair of electrodes of the sensor cell, the specific gas component and remaining oxygen in the chamber are decomposed to be externally exhausted. Since the chamber is controlled by the pump cell to have a predetermined oxygen concentration, the current value of the current flowing at this time varies depending upon the concentration of the specific gas component. Therefore, the concentration of the specific gas component can be detected based on this current value.

In the detector according to an eleventh aspect of the invention, the monitor cell includes a solid electrolyte body having oxygen ion conductivity and a pair of electrodes formed on surfaces of the solid electrolyte body. Furthermore, a concentration of remaining oxygen in the chamber is detected based on a current value of the current flowing between the pair of electrodes or based on the electromotive force generated between the pair of electrodes when a predetermined voltage is applied to the pair of electrodes.

When a predetermined voltage is applied to the pair of electrodes of the monitor cell, only remaining oxygen in the chamber is decomposed to be externally exhausted. Therefore, a concentration of remaining oxygen can be detected based on a current value of a current flowing at this time. Alternatively, since electromotive force is generated between the pair of electrodes of the monitor cell in accordance with a difference in oxygen concentration therebetween, the concentration of remaining oxygen can also be detected based on the electromotive force.

In the detector according to a twelfth aspect of the invention, the concentration of the specific gas component in the gas to be measured is detected based on a difference in output between the sensor cell and the monitor cell. Since an output in accordance with the specific gas component and the concentration of remaining oxygen can be obtained from the sensor cell, whereas an output in accordance with the concentration of remaining oxygen can be obtained from the monitor cell, a difference in output between the sensor cell and the monitor cell is obtained so as to obtain an output independent of the oxygen concentration, thereby enabling accurate detection. At this time, if the cells have different responses to oxygen, a difference in output is varied. As a result, there is a possibility that a detected value may also be varied. In the present invention, however, since the output responses of the cells can be made to substantially match each other by the electrical correction means, the detection accuracy is further improved.

In the detector according to a thirteenth aspect of the invention, the sensor cell and the monitor cell are provided in the chamber so as to be close to each other. When the monitor cell and the sensor cell are provided so as to be close to each other, an oxygen concentration detected in the monitor cell essentially reflects an oxygen concentration on the sensor cell even if an oxygen distribution is generated in the chamber. Therefore, the effects of the oxygen distribution in the chamber can be reduced to enable more accurate detection.

In the detector according to a fourteenth aspect of the invention, the specific gas component is NOx, and the electrode of the sensor cell, which is provided so as to face the chamber, is made of an electrode material reactive to reductions of NOx, whereas the electrode of the monitor cell, which is provided so as to face the chamber, is made of an electrode material inactive to reduction of NOx. For example, in the case where an NOx concentration is to be detected, when a Pt-Rh electrode or the like, which is active to NOx decomposition, is used as the electrode of the sensor cell, whereas a Pt—Au electrode or the like, which is inactive to NOx decomposition, is used as the electrode of the monitor cell, the NOx concentration can be accurately detected based on a difference in output between the sensor cell and the monitor cell. Moreover, an EGR system, that is, a catalyst system and the like, can be effectively controlled by using the detection result.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1A:
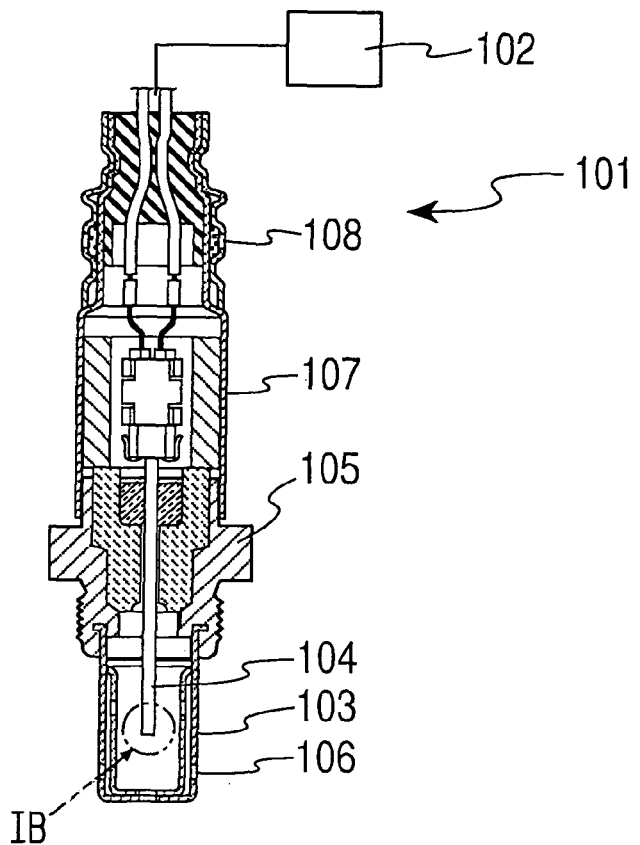
FIG. 1A is a cross-sectional view of a general configuration of the gas concentration detector according to a first embodiment of the invention.

The following description of the preferred embodiment(s) is merely exemplary in nature and is in no way intended to limit the invention, its application, or uses. Hereinafter, a first embodiment of the present invention will be described with reference to FIGS. 1A to 4. As shown in FIG. 1A, a gas concentration detector of the present invention is constituted by an NOx sensor 101 and a control circuit 102. For example, the gas concentration detector is placed in an exhaust pipe 202 of an internal combustion engine (diesel engine) 200 shown in FIG. 2 so as to detect a concentration of NOx (specific gas component) in an exhaust gas (gas to be measured). The internal combustion engine 200 includes a common rail 203 which is common to all of the cylinders. With such a configuration, a high-pressure fuel accumulated in the common rail 203 is injected into the corresponding cylinder by a fuel injection valve 204. Moreover, an EGR path 206 for connecting an exhaust manifold 205 and an intake manifold 207 with each other is provided so that part of an exhaust gas is returned to an intake air through the ERG path 206.

In the exhaust pipe 202 following the exhaust manifold 205, a post-treatment device 209 carrying an NOx storage-reduction catalyst and an oxidation catalyst 210 are provided. An exhaust gas fuel addition valve 208 for adding a fuel serving as an NOx reducing agent is provided for the exhaust manifold 205. The NOx sensor 101 of the present invention, which is placed upstream of the oxidation catalyst 210, takes in exhaust gas after the exhaust gas passes through the NOx storage-reduction catalyst. Then, the control circuit 102 detects an NOx concentration based on a signal from the NOx sensor 101 to output a detected value to an ECU 201. The ECU 201 performs, for example, degradation diagnosis of the NOx storage-reduction catalyst or feedback control of the EGR system, based on the detected NOx concentration.

Figure 2:
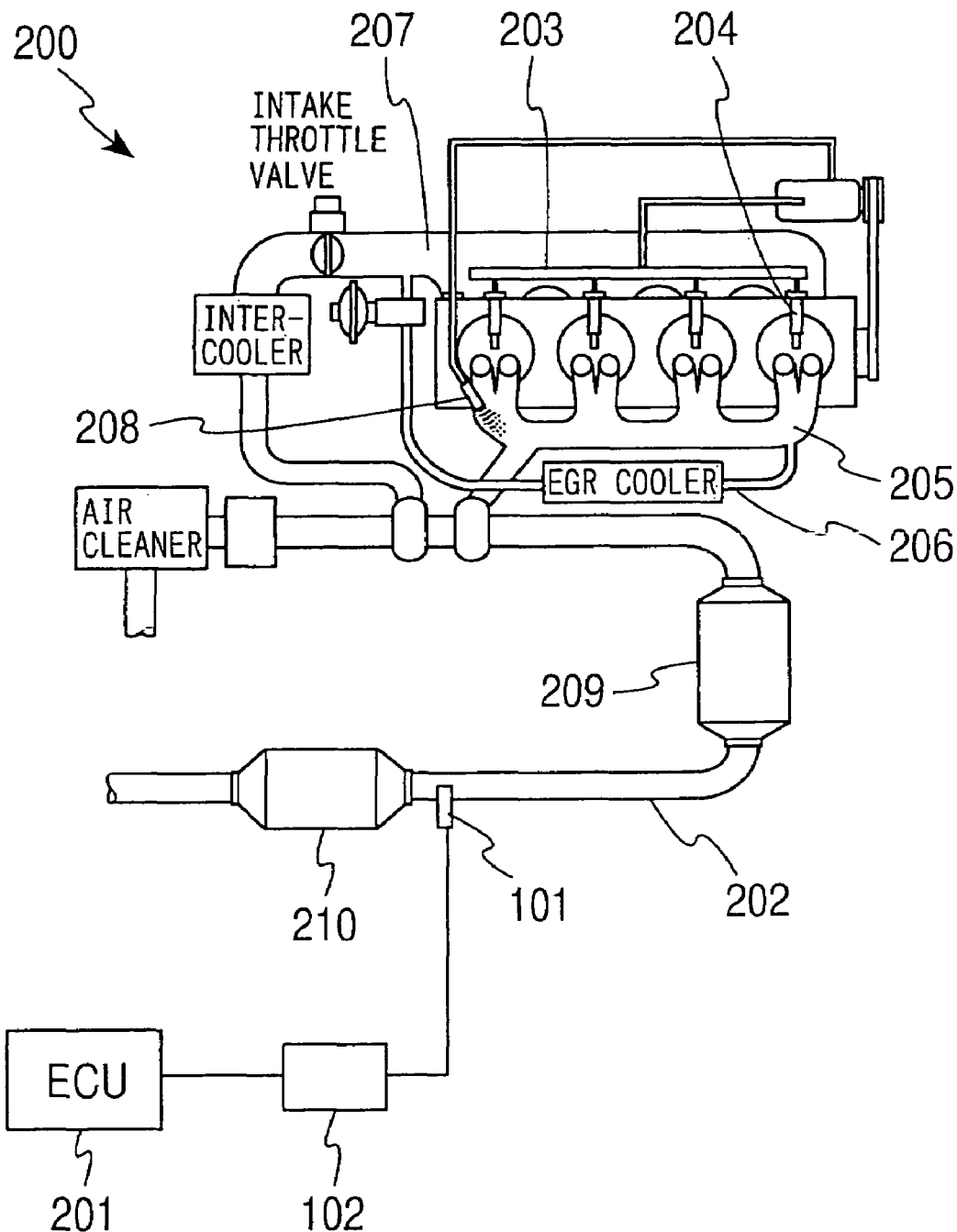
FIG. 2 is a schematic configuration view of an internal combustion engine to which the gas concentration detector according to an embodiment of the present invention is applied.

In FIG. 1A, the NOx sensor 101 includes a cylindrical housing 105 fixed to a wall of the exhaust pipe 202 (FIG. 2). A sensor element 104 is held in the cylindrical housing 105 in an insulated manner. A tip of the sensor element 104 (a lower end in FIG. 1A) is housed within an element cover 103 which is fixed on a lower end of the housing 105 to project into the exhaust pipe 202. The element cover 103 has a double structure composed of an inner cover and an outer cover. The exhaust gas in the exhaust pipe 202 is taken up through exhaust ports 106 provided on a side and bottom wall. At an upper end of the housing 105, a cylindrical member 107 having an atmospheric port 108 on its side wall is fixed.

Figure 1B:
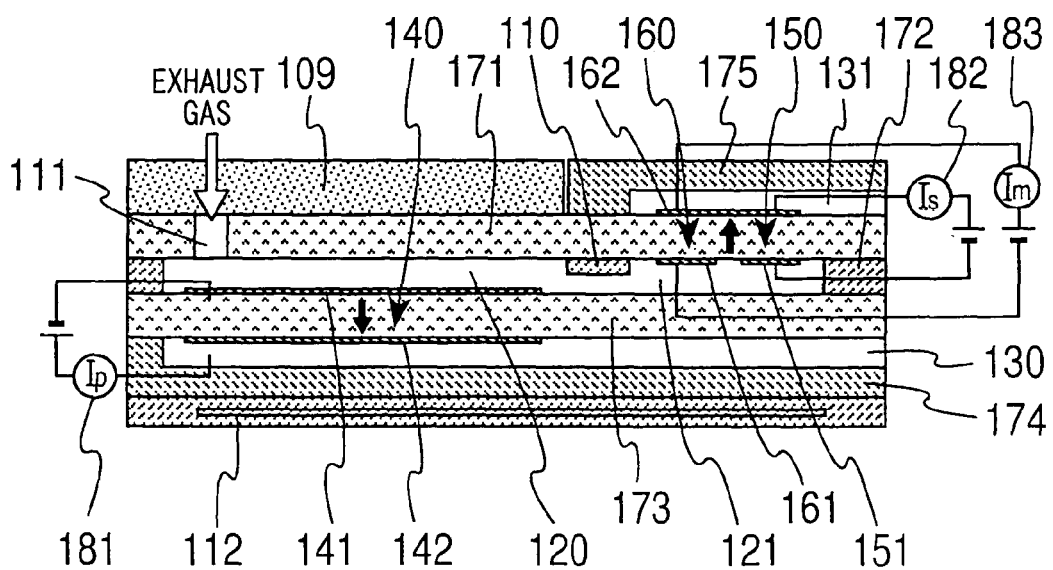
FIG. 1B is an enlarged, schematic, cross-sectional view of portion 1B in FIG. 1A of a tip of a sensor element of an NOx sensor according to a first embodiment of the invention.

FIG. 1B is an enlarged view of the tip of the sensor element 104. The sensor element 104 has a first chamber 120 and a second chamber 121 into which an exhaust gas is introduced. It also has atmospheric paths 130, 131 in communication with the atmosphere, a pump cell 140 provided on the first chamber 120 side, and a sensor cell 150 and a monitor cell 160 provided on the second chamber 121 side. The sensor cell 150 and the monitor cell 160 are provided so as to be adjacent to each other in a longitudinal direction of the sensor element 104. The first chamber 120 is in communication with the second chamber 121 through a throttle 110. An exhaust gas is introduced into the first chamber 120 through a porous diffusion layer 109 and a pin hole 111.

The sensor element 104 is constituted by the following structure. A sheet-like solid electrolyte body 173 constituting the pump cell 140 is laminated below a sheet-like solid electrolyte body 171 constituting the sensor cell 150 and the monitor cell 160 through a spacer 172 constituting the first chamber 120 and the second chamber 121. Then, a spacer 174 constituting the atmospheric path 130 and a sheet-like heater 112 are laminated below the sheet-like solid electrolyte body 173. Above the solid electrolyte body 171, a spacer 175 constituting the porous diffusion layer 109 and the atmospheric path 131 is laminated. The solid electrolyte bodies 171, 173 are formed of a solid electrolyte having oxygen ion conductivity, such as zirconia, whereas the spacers 172, 174, and 175 are made of an insulating material such as alumina. The porous diffusion layer 109 is made of a porous alumina or the like.

The pump cell 140 is constituted by the solid electrolyte body 173 and a pair of electrodes 141, 142 which are provided on the upper and lower surfaces of the solid electrolyte body 173 so as to be opposed to each other. The pump cell 140 exhausts or pumps oxygen into the exhaust gas, which is introduced into the first chamber 120, to the atmospheric path 130 so as to adjust oxygen concentration in the first chamber 120. For the pair of electrodes, an electrode that is inactive to a reduction of NOx, for example, a Pt-Au porous cermet electrode, is suitably used as the electrode 141 on the first chamber 120 side, whereas a Pt porous cermet electrode is suitably used as the electrode 142 on the atmospheric path 130 side. The porous cermet electrodes are formed by pasting and baking a metal component and ceramic such as zirconia or alumina.

The monitor cell 160 is constituted by the solid electrolyte body 171 and a pair of electrodes 161, 162 which are provided on the upper surface and the lower surface of the solid electrolyte body 171 so as to be opposed to each other. A concentration of. remaining oxygen in the exhaust gas introduced from the first chamber 120 via the throttle 110 to the second chamber 121 is detected by the monitor cell 160. For the pair of electrodes, an electrode that is inactive to reduction of NOx, for example, a Pt-Au porous cermet electrode, is suitably used as the electrode 161 on the second chamber 121 side, whereas, for example, a Pt porous cermet electrode is suitably used as the electrode 162 on the atmospheric path 131 side. A predetermined voltage is applied between the electrodes 161, 162 to obtain a current output in accordance with a concentration of remaining oxygen.

The sensor cell 150 is constituted by the solid electrolyte body 171 and a pair of electrodes 151, 162 provided on the upper surface and the lower surface of the solid electrolyte body 171 so as to be opposed to each other. The sensor cell 150 is provided so as to be adjacent to the monitor cell 160. For the pair of electrodes, the electrode 162 on the atmospheric path 131 side is a common electrode to the monitor cell 160. The sensor cell 150 detects an NOx concentration and a concentration of remaining oxygen in the exhaust gas introduced into the second chamber 121. As the electrode 151 on the second chamber 121 side, an electrode active to reduction of NOx, for example, a Pt—Rh porous cermet electrode, is used. A predetermined voltage is applied between the electrodes 151, 162 to obtain a current output in accordance with an NOx concentration and a concentration of remaining oxygen.

The heater 112 is formed by embedding a heater electrode in a sheet made of an insulating material such as alumina. The heater electrode generates heat when being externally supplied with electric power to heat the entire sensor element, thereby keeping each of the above-mentioned cells 140, 150, and 160 at or above an activation temperature.

The principal of operation of the NOx sensor 101 having the above structure will be described. In FIG. 1B, an exhaust gas, which is a gas to be measured, is introduced into the first chamber 120 through the porous diffusion layer 109, and the pin hole 111. The amount of the introduced gas is determined by a diffusion resistance of the porous diffusion layer 109 and the pin hole 111. When a voltage is applied to the electrodes 141, 142 of the pump cell 140 so that the electrode 142 on the atmospheric path 130 side serves as a positive (+) electrode, oxygen in the exhaust gas is reduced on the electrode 141 on the first chamber 120 side to be oxygen ions, which are in turn exhausted by a pumping action toward the electrode 142 (in a direction indicated with a downward arrow in FIG. 1B). When the direction of the applied voltage is reversed, oxygen is introduced from the atmospheric path 130 side to the first chamber 120 side.

The pump cell 140 utilizes this oxygen pumping action to pump and exhaust oxygen while adjusting the magnitude and the direction of the applied voltage so as to control the oxygen concentration in the chamber. Normally, in order to reduce the effect of oxygen at the detection of NOx, oxygen introduced into the first chamber 120 is exhausted to keep the second chamber 121 at a predetermined low oxygen concentration. Moreover, since the electrode 141 on the first chamber 120 side is an electrode inactive to NOx, NOx in the exhaust gas is not decomposed in the pump cell 140.

In this embodiment, the pump cell 140 is controlled by using an applied voltage map which is determined in advance in accordance with a pump cell current Ip measured by a current detector 181. The pump cell 140 has a limiting current characteristic with respect to the oxygen concentration. In a V–I characteristic view showing the relation between a pump cell applied voltage Vp and the pump cell current Ip, a limiting current detection range corresponds to a linear section approximately parallel to a V axis. The limiting current detection range shifts in a direction in which the voltage value increases as the oxygen concentration becomes higher. Therefore, the pump cell applied voltage Vp is variably controlled in accordance with the pump cell current Ip to quickly exhaust oxygen introduced into the first chamber 120, thereby controlling the first chamber 120 to have a predetermined low oxygen concentration. As a result, the effects of oxygen acting as an interference gas at the detection of NOx corresponding to a specific gas in the present invention can be reduced.

The exhaust gas passing through the vicinity of the pump cell 140 flows into the second chamber 121 in communication with the first chamber 120 through the throttle 110. A slight amount of oxygen remaining in the exhaust gas is reduced to be oxygen ions on the electrode 161 on the second chamber 121 side when a predetermined voltage is applied between the electrodes 161, 162 of the monitor cell 160 so that the electrode 162 on the atmospheric path 131 side serves as a positive (+) electrode. Then, oxygen ions are exhausted toward the electrode 162 by the pumping action (in a direction indicated with an upward arrow in FIG. 1B). Since the electrode 161 is an electrode inactive to NOx, a monitor cell current Im measured by a current detector 183 depends on the amount of oxygen reaching the electrode 161 in the second chamber 121, not on the amount of NOx. Therefore, the detection of the monitor cell current Im allows the detection of a concentration of remaining oxygen.

In the sensor cell 150, on the other hand, the electrode 151 on the second chamber 121 side is an electrode active to NOx. Remaining oxygen and NOx in the exhaust gas are reduced to be oxygen ions on the electrode 161 on the second chamber 121 side when a predetermined voltage is applied between the electrodes 151, 162 so that the electrodes 162 on the atmospheric path 131 side serves as a positive (+) electrode. Then, the oxygen ions are exhausted toward the electrode 162 by the pumping action (in a direction indicated with the upward arrow in FIG. 1B). Therefore, a sensor cell current Is measured by a current detector 182 depends on the amount of oxygen and the amount of NOx reaching the second chamber 121.

The sensor cell 150 and the monitor cell 160 are adjacent to each other in the second chamber 121, and therefore the amount of oxygen reaching the electrode 151 on the second chamber 121 side is substantially equal to that reaching the electrode 161 on the second chamber 121 side. Accordingly, the subtraction of the monitor cell current Im (corresponding to the oxygen concentration) from the sensor cell current Is allows the detection of the NOx concentration.

As described above, when the NOx concentration is detected by using a difference in output between the sensor cell 150 and the monitor cell 160, which are provided adjacent to each other, an output independent of the amount of oxygen in the chambers can be obtained. In practice, however, since the material of the electrode 151 (Pt—Rh) of the sensor cell 150 differs from that of the electrode 161 (Pt—Au) of the monitor cell 160 on the second chamber 121 side, a difference between these electrodes is generated in reactivity (responsibility) to oxygen. In particular, the sensor cell 150 is likely to take up oxygen due to oxygen storage ability of Rh, and therefore becomes insensitive to variations in oxygen concentration.

Accordingly, in the present invention, an electrical correction means for substantially matching output responses of the sensor cell 150 and the monitor cell 160 with each other to a variation in oxygen concentration is provided. In order to realize such means, output of the monitor cell 160 is corrected through means for restraining an electrical reaction, for example, through a filter, in this embodiment. A specific frequency component is passed or removed through the filter to smooth a frequency response of the monitor cell current Im, thereby eliminating a difference in reactivity (response) to oxygen.

Figure 3A:
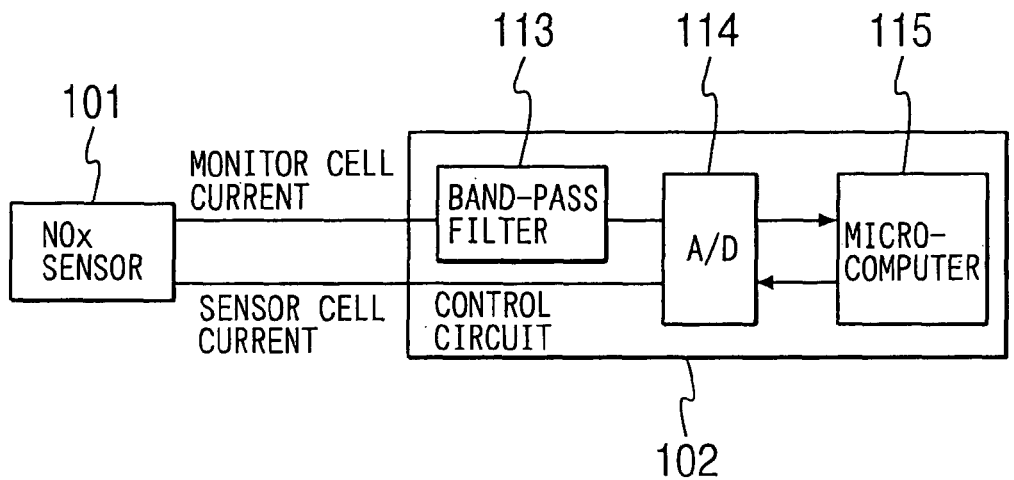
FIG. 3A is a view showing a control circuit configuration in the gas concentration detector according to the first embodiment.
Figure 4A:
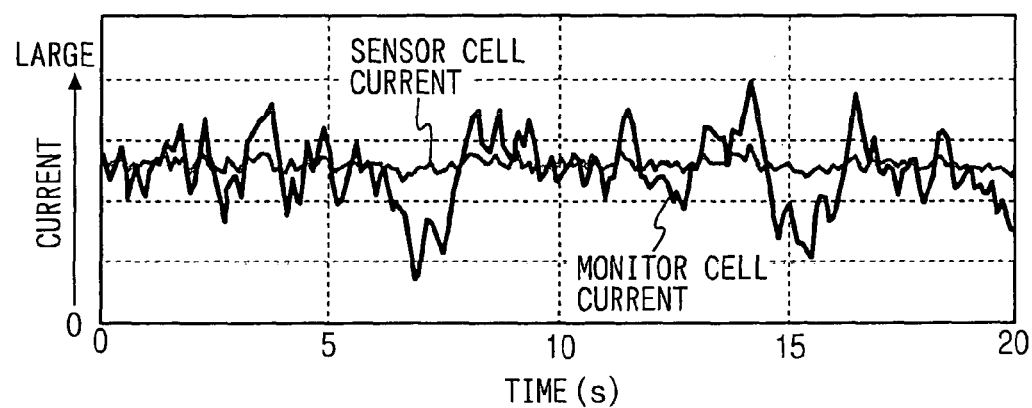
FIG. 4A is a graph of output characteristic of a sensor cell current and a monitor cell current measured when using a model gas.
Figure 4B:
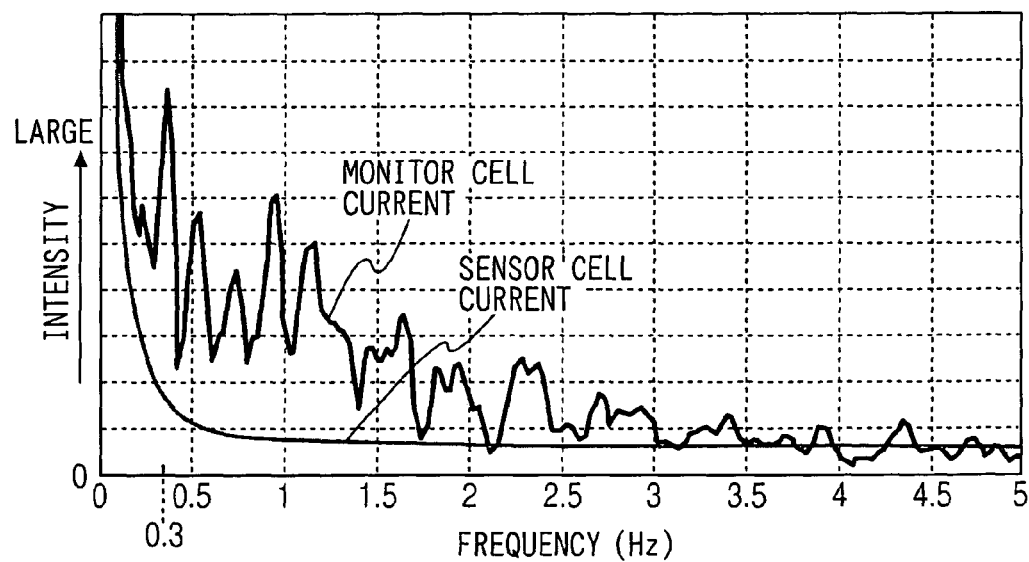
FIG. 4B is a graph showing the results of an FFT analysis of the sensor cell current and the monitor cell current.

Specifically, as shown in FIG. 3A, a band-pass filter 113 is provided in the control circuit 102 so as to pass only a specific frequency component of the monitor cell current Im measured by the current detector 183. A pass band of the band-pass filter 113 is set, for example, based on the result of frequency analysis of output characteristics of the sensor cell 150 and the monitor cell 160 obtained by using a model gas. FIG. 4A is a graph showing raw outputs of the sensor cell current Is and the monitor cell current Im, and FIG. 4B is a graph showing the results of FFT analysis on the sensor cell current Is and the monitor cell current Im. As can be seen from FIG. 4A, it is understood that the monitor cell current Im is widely varied as compared with the sensor cell current Is. This is because the monitor cell 160 more sensitively reacts to a variation in oxygen concentration caused by an oxygen concentration distribution and the like. In order to restrain such a wide variation in the monitor cell current Im, it is sufficient to set limits at about 2.5 Hz on the high frequency side and at about 0.3 Hz on the low frequency side for determining a region where a difference in intensity is large so that the filter eliminates signal frequency components in the range of 0.3 Hz to 2.5 Hz.

Figure 3B:
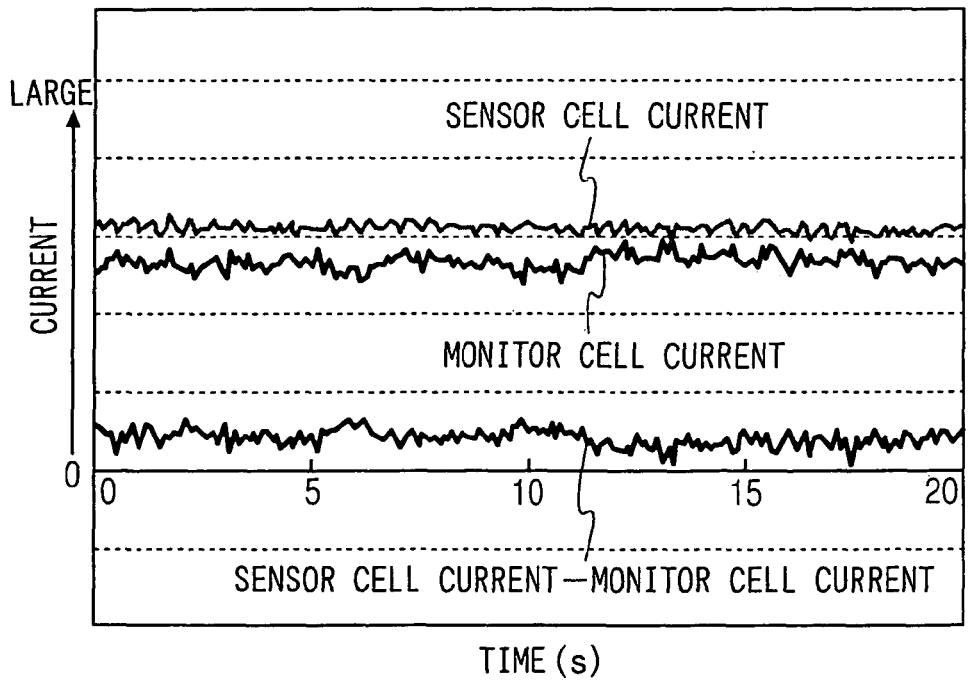
FIG. 3B is a graph showing a monitor cell current after passing through a filter, a sensor cell current, and the difference between the two currents.

The control circuit 102 fetches a current output of the monitor cell 160, which passes through the band-pass filter 113 and into a microcomputer 115 via an A/D converter 114, while fetching the sensor cell current Is, which is measured by the current detector 182, and then passes it via the A/D converter 114 into the microcomputer 115. Then, the control circuit 102 subtracts the monitor cell current Im from the sensor cell current Is to calculate an NOx concentration. FIG. 3B is a graph showing the monitor cell current Im after passing through the filter, the sensor cell current Is, and a difference between these currents. It is understood that the monitor cell current Im is stabilized to substantially match the response of the monitor cell current Im with that of the sensor cell current Is. As a result, the NOx concentration represented by a difference between the monitor cell current Im and the sensor cell current Is can be accurately detected.

Although the band-pass filter is used as the electrical correction means in the above-described first embodiment, any other filter can be used as long as it is capable of passing or removing only a specific frequency component in accordance with its use and required characteristics. For example, a low-pass filter, a high-pass filter, a band-stop filter and the like can be cited as examples of other available filters. Alternatively, any other means for restraining an electrical reaction so as to substantially match the output response of the sensor cell 150 with that of the monitor cell 160 to a variation in oxygen concentration can also be used.

Next, a second embodiment of the present invention will be described with reference to FIGS. 5, 6A and 6B. Since the structure and the basic operation of the NOx sensor 101 in this second embodiment are similar to those of the first embodiment described above, the main differences between these two embodiments will be described below. In this embodiment, instead of providing the band-pass filter 113 in the control circuit 102, a signal processing means for performing smoothing correction on the outputs of the sensor cell 150 and the monitor cell 160 is provided as an electrical correction means. In this case, a smoothing constant N is variably set based on an amplitude L and a cycle T of a pulsation of each of the output currents of the sensor cell 150 and the monitor cell 160. By performing the smoothing correction using the smoothing constant N set for each of the output currents, the amplitude and phase of the monitor cell current Im and those of the sensor cell current Is can be made to match each other.

Figure 5:
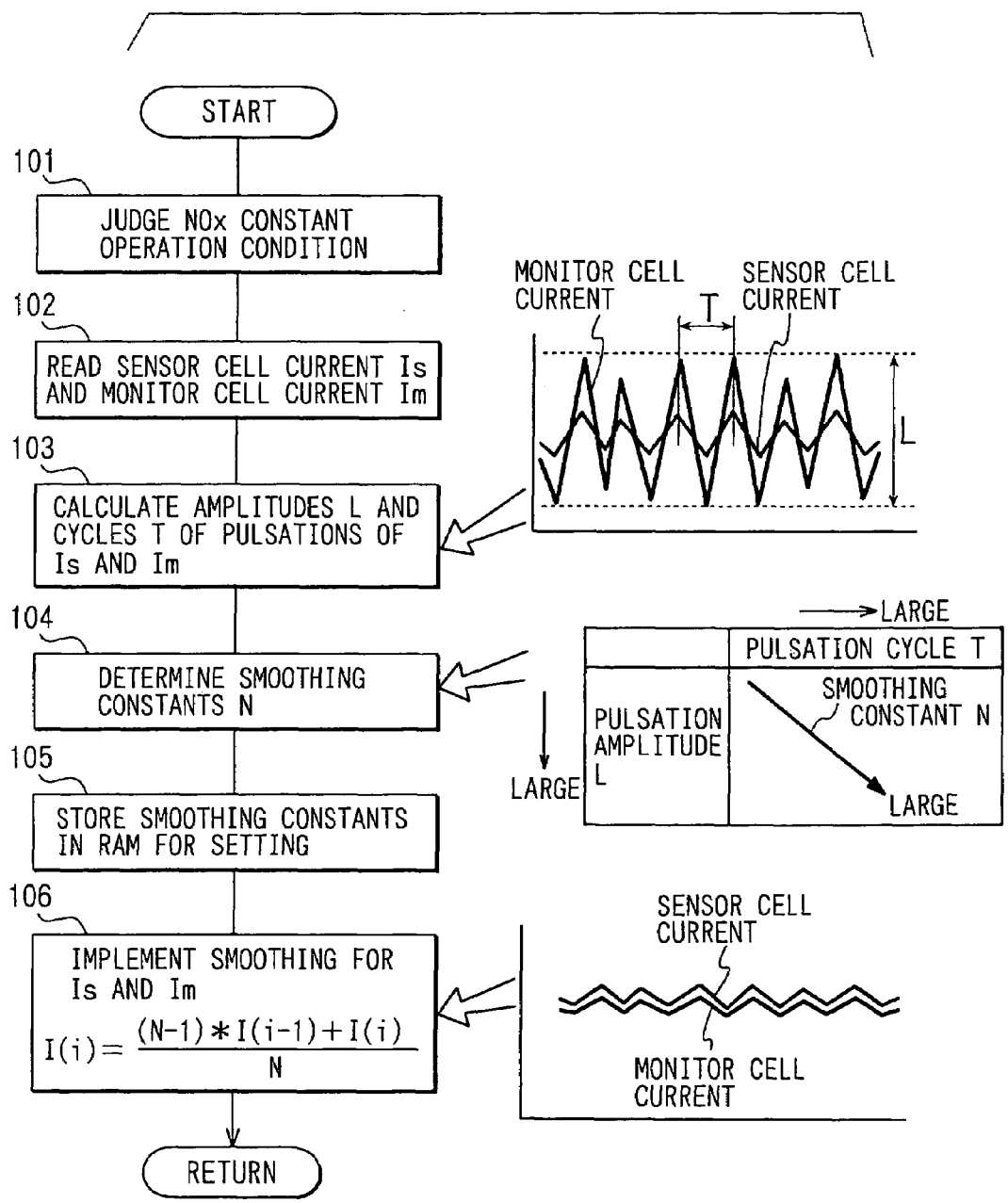
FIG. 5 is a flowchart exhibiting a smoothing correction according to a second embodiment.
Figure 6A:
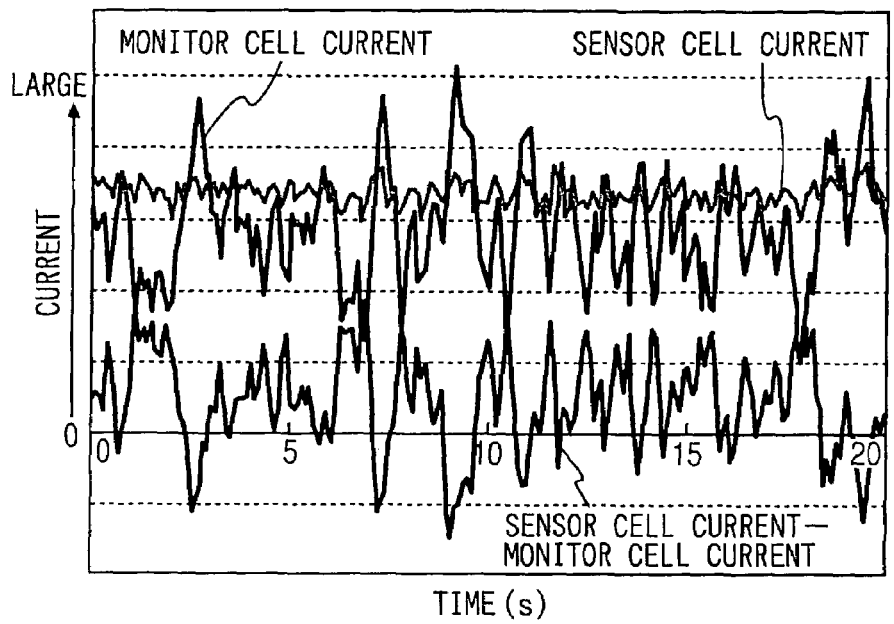
FIG. 6A is an output characteristic view of the sensor cell current and the monitor cell current without smoothing correction.
Figure 6B:
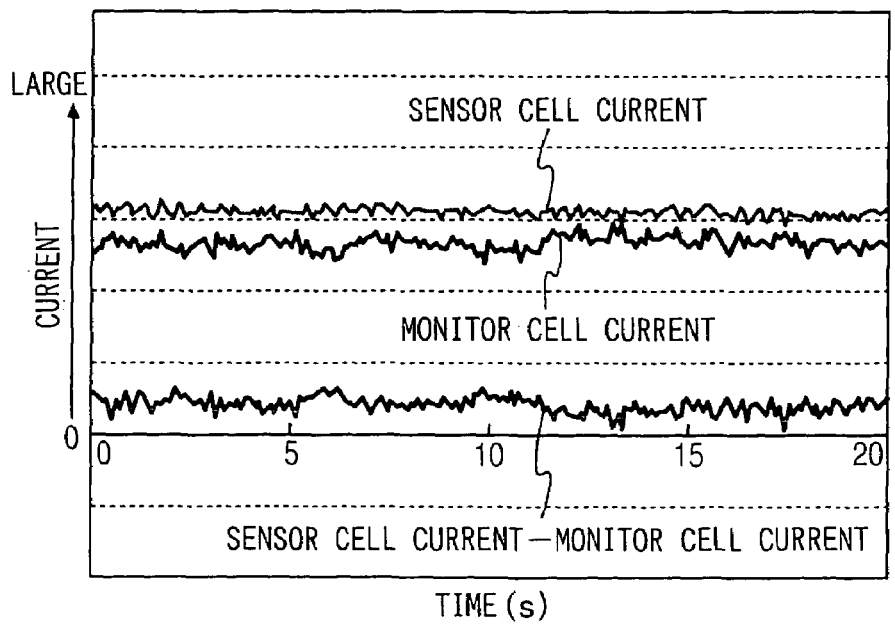
FIG. 6B is an output characteristic view of the sensor cell current and the monitor cell current with smoothing correction.

Specifically, in the microcomputer 115 functioning as a signal processing means, processing shown in the flowchart of FIG. 5 is executed. In FIG. 5, after the start of the processing, it is first determined whether the internal combustion engine 200 is in an operating state with a constant NOx concentration at step S101. The operating state with a constant NOx concentration means, for example, a condition under which the amount of exhausted NOx becomes 0 after elapse of a predetermined amount of time from cutting the fuel. Under such a condition, variations in combustion and factors of varying NOx due to an EGR and the like can be eliminated. If it is determined that the internal combustion engine 200 is in the operating state with a constant NOx concentration at step 101, the processing proceeds to step 102 where the sensor cell current Is and the monitor cell current Im, respectively measured by the current detectors 182, 183, are read into the microcomputer 115 via the A/D converter 114.

Next, at step 103, the amplitude L and the cycle T of a pulsation of each of the sensor cell current Is and the monitor cell current Im are calculated. Then, at step 104, the smoothing constants N of the sensor cell current Is and the monitor cell current Im are respectively determined based on the calculated amplitudes L and the cycles T. Herein, the relation between the amplitude L and the cycle T, and the smoothing constant N is pre-recorded in the microcomputer 115 as map data. As shown in FIG. 5, the smoothing constant N is set so as to be larger as the amplitude L or the cycle T increases.

After the thus determined smoothing constants N are stored in a RAM for setting at step 105, smoothing correction on the sensor cell current Is and the monitor cell current Im are implemented by using the smoothing constants N according to the following formula (1).

$$I(i)=\{(N-1)*I(i-1)+I(i)\}/N \quad (1)$$

When the smoothing constants N are variably set for the sensor cell current Is and the monitor cell current Im, respectively, so as to correct the outputs, the amplitudes and the phases of the sensor cell current Is and the monitor cell current Im can be made to match each other. FIG. 6A illustrates the monitor cell current Im, the sensor cell current Is, and a difference between these currents without smoothing correction. FIG. 6B illustrates those with smoothing correction. From these graphs, it is understood that a deviation in output due to a difference in responses between the monitor cell current Im and the sensor cell current Is is eliminated by executing the processing in this embodiment. As a result, the pulsation is eliminated in a difference between these currents, which represents the NOx concentration, thereby enabling accurate detection of the NOx concentration.

Although the smoothing correction in accordance with the formula (1) above is performed in the second embodiment described above, it is also possible to perform signal processing in which the number of moving averages is variably set to average the outputs. In such a case, the number of averaging processings is set to be larger as the amplitudes and the cycles of pulsations of the sensor cell current Is and the monitor cell current Im are increased so as to substantially match the responses of the monitor cell current Im and the sensor cell current Is with each other. As a result, the same effects of improving detection accuracy as those described above can be obtained.

As described above, the electrical correction means using a hardware approach or a software approach is provided in the NOx sensor where the sensor cell 150 and the monitor cell 160 have different oxygen reactivities so as to substantially match the current output responses of the sensor cell 150 and the monitor cell 160 with each other. As a result, the detection accuracy for NOx can be remarkably improved. In particular, if the present invention is applied to a detector using a difference in output between the sensor cell 150 and the monitor cell 160 as a detected value as in the case of each of the above-described embodiments, a deviation in output due to a difference in responses can be eliminated. Therefore, the present invention is more effectively applied.

Figure 7A:
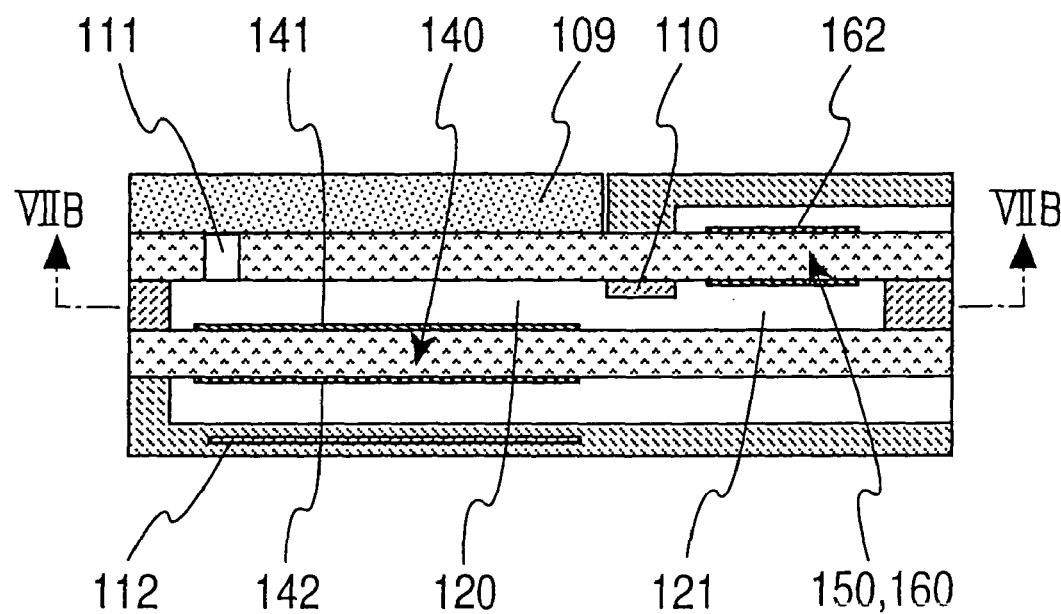
FIG. 7A is a schematic cross-sectional view showing a tip of a sensor element of an NOx sensor according to a third embodiment of the present invention.
Figure 7B:
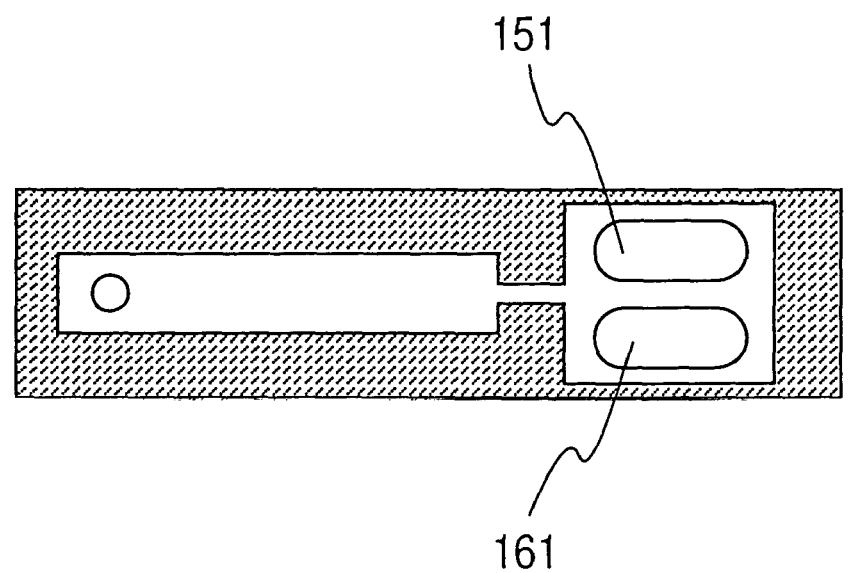
FIG. 7B is a cross-sectional view taken along the line VIIB—VIIB in FIG. 7A according to a third embodiment of the present invention.

The structure of the NOx sensor 101 is not limited to those of the first and second embodiments described above (FIGS. 1A and 1B). For example, a structure illustrated in FIGS. 7A and 7B presented as the third embodiment of the present invention can also be used. Although the sensor cell 150 and the monitor cell 160 are provided so as to be adjacent to each other in a longitudinal direction of the sensor element in the first and second embodiments, the sensor cell 150 and the monitor cell 160 are substantially symmetrically provided at the same position in a longitudinal direction of the sensor element 104 in the sensor element 104 according to the third embodiment as shown in FIGS. 7A and 7B. The other structures and the basic operations are the same or similar to those of the first and second embodiments.

An oxygen concentration distribution in the second chamber 121 is likely to be generated in a direction along an introduction path of the exhaust gas, in this case, in a longitudinal direction of the sensor element. With the arrangement according to the third embodiment, however, the sensor cell 150 and the monitor cell 160 are placed at the same position with respect to a gas flow in the second chamber 121. Therefore, the oxygen concentration on the electrode 151 of the sensor cell 150 and that on the electrode 161 of the monitor cell 160 become equal to each other, independently of the oxygen concentration distribution. Accordingly, the sensor cell 150 and the monitor cell 160 are made to have the same sensitivity to remaining oxygen in the second chamber 121, thereby enabling more accurate detection.

Figure 8:
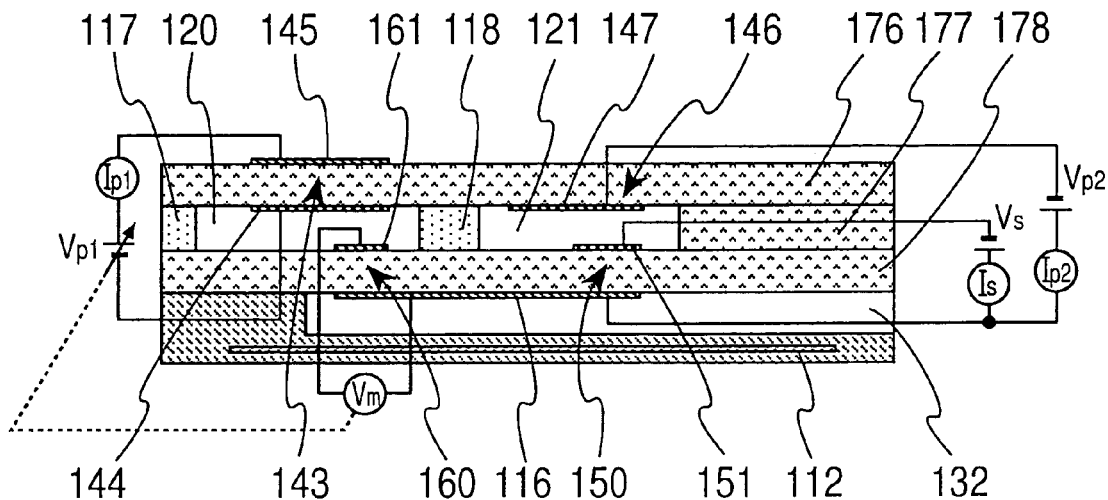
FIG. 8 is a schematic cross-sectional view of a tip of a sensor element of an NOx sensor according to a fourth embodiment.

Moreover, although the NOx sensor 101 for detecting NOx based on a difference in current output between the sensor cell 150 and the monitor cell 160 is used in the above-described embodiments, the present invention can be applied to other NOx sensors 101, which will be shown in FIG. 8 as a fourth embodiment.

In FIG. 8, the solid electrolyte bodies 176, 177, and 178, each being made of zirconia or the like, are successively laminated to form the sensor element 104. In the sensor element 104, the first chamber 120 and the second chamber 121 are formed. An exhaust gas is introduced through porous resistance layers 117, 118 and into the first chamber 120 and the second chamber 121. A first pump cell 143 and the monitor cell 160 are provided in the first chamber 120, whereas the sensor cell 150 and a second pump cell 146 are provided in the second chamber 121. The first pump cell 143 has a pair of electrodes 144, 145 formed on the upper surface and the lower surface of the solid electrolyte body 176. The monitor cell 160 has a pair of electrodes 161 and 116 formed on the upper surface and the lower surface, respectively, of the solid electrolyte body 178. The electrode 116 is an atmospheric electrode facing the atmospheric path 132 and serves as a common electrode to the sensor cell 150 and the second pump cell 146. The sensor cell 150 has a pair of electrodes 151, 116 formed on the upper surface and the lower surface, respectively, of the solid electrolyte body 178. The second pump cell 146 is constituted by the electrode 147 on the lower surface of the solid electrolyte body 176 and the atmospheric electrode 116. The heater 112 is provided below the atmospheric path 132.

In the above structure, an exhaust gas is introduced into the first chamber 120 through the porous resistance layer 117. Most of the oxygen in the gas is exhausted to the exhaust side by the first pump cell 143. At this time, an oxygen concentration in the first chamber 120 is detected based on electromotive force Vm generated between the electrodes 161, 116 of the monitor cell 160. A voltage Vp1 applied to the first pump cell 143 is controlled so that a detected value becomes a predetermined constant value. As a result, the first chamber 120 has a predetermined low oxygen concentration. The exhaust gas is further introduced into the second chamber 121 through the porous resistance layer 118. Remaining oxygen in the gas is decomposed by the second pump cell 146 to be exhausted to the atmospheric path 132. A voltage Vp2 applied to the second pump cell 146 is controlled in accordance with a current Ip2 flowing through the second pump cell 146. A predetermined voltage Vs is applied to the sensor cell 150 so that NOx is decomposed on the electrode 151 on the chamber side to be exhausted to the atmospheric path 132. At this time, the current Is flowing through the sensor cell 150 is detected as an NOx concentration.

As described above, also in the structure for controlling the voltage Vp1 applied to the first pump cell 143 by the voltage output (Vm) of the monitor cell 160, the electrical correction means described in the first and second embodiments can be used. In the fourth embodiment, the voltage Vp1 applied to the first pump cell 143 is controlled by the voltage output (Vm) of the monitor cell 160. In this point, the fourth embodiment differs from the first and second embodiments described above where a difference in output between the monitor cell 160 and the sensor cell 150 is calculated to obtain the NOx concentration. However, output characteristics of the sensor cell 150 and the monitor cell 160 (for example, an oxygen concentration is indicated on the ordinate axis, whereas time is indicated on the abscissa axis) are substantially the same as those in FIG. 4A.

Specifically, the monitor cell 160 has a high reactivity to oxygen. Therefore, if the first pump cell 143 is controlled based on the reactivity of the monitor cell 160, the oxygen concentration in the first chamber 120 is not stabilized. As a result, there exists a possibility that the output of the sensor cell 150 may be affected. Accordingly, also in this embodiment, the output of the monitor cell 160 is smoothed by using the electrical correction means described in the first and second embodiments, whereby the same effects of improving the detection accuracy can be obtained.

Figure 9:
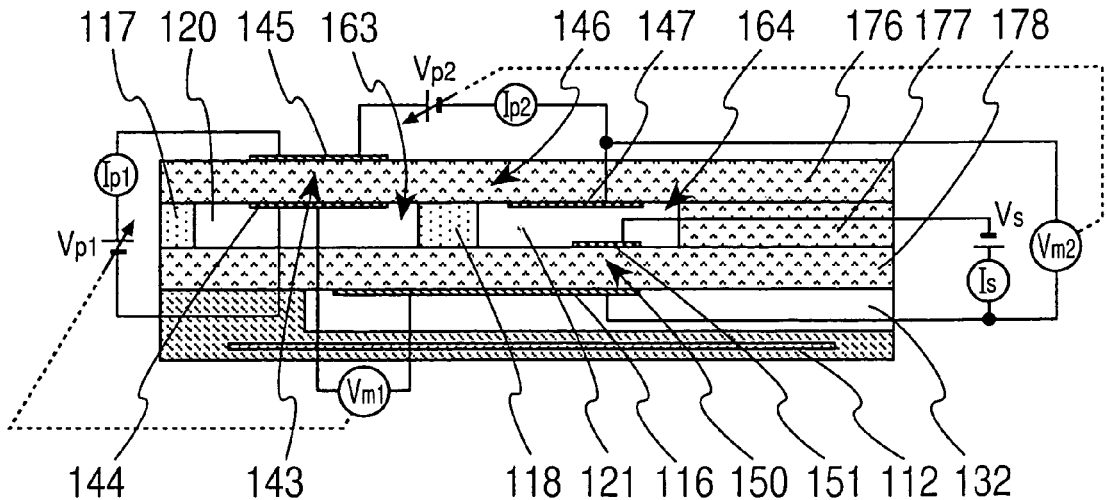
FIG. 9 is a schematic cross-sectional view of a tip of a sensor element of an NOx sensor according to a fifth embodiment.

FIG. 9 shows a fifth embodiment of the present invention. The structure of the fifth embodiment is substantially the same as that of the fourth embodiment except that a first monitor cell 163 is provided in the first chamber 120 and a second monitor cell 164 is provided in the second chamber 121. The first monitor cell 163 has the electrode 144 common to the first pump cell 143 and the atmospheric electrode 116, whereas the second monitor cell 164 has the electrode 147 common to the second pump cell 146 and the atmospheric electrode 116.

In this embodiment, an oxygen concentration in the first chamber 120 is detected based on electromotive force Vm1 generated between the electrodes 144, 116 of the first monitor cell 163 so as to control the voltage Vp1 applied to the first pump cell 143. Simultaneously, an oxygen concentration in the second chamber 121 is detected based on electromotive force Vm2 generated between the electrodes 147, 116 of the second monitor cell 164 so as to control the voltage Vp2 applied to the second pump cell 146. The electrical correction means described in the above first and second embodiments can also be used in this structure. As a result, the same effects can be obtained.

In each of the above-described embodiments, the structures, in which the present invention is applied to detection of a concentration of NOx contained in an exhaust gas, have been described. However, the present invention is also applicable to a gas concentration detector for detecting a specific gas component other than NOx. Moreover, a gas other than an exhaust gas from an internal combustion engine can be measured using the present invention.

What is claimed is:

1. A gas concentration detector comprising:
a sensor cell, wherein the sensor cell detects a concentration of a specific gas component in a gas to be measured when the gas is introduced into a chamber;
a monitor cell, wherein the monitor cell detects an oxygen concentration in the chamber, and the sensor cell and the monitor cell have different oxygen reactivities; and
electrical correction means for substantially matching output responses of the sensor cell and the monitor cell to a variation in oxygen concentration with each other.

2. The gas concentration detector according to claim 1, wherein means for restraining an electrical reaction of at least one of the sensor cell and the monitor cell is provided as the electrical correction means.

3. The gas concentration detector according to claim 2, wherein the means for restraining the electrical reaction is a filter for passing or removing a specific frequency component in an output of any one of the sensor cell and the monitor cell.

4. The gas concentration detector according to claim 3, wherein the means for restraining the electrical reaction is a band-pass filter.

5. The gas concentration detector according to claim 1, wherein signal processing means for correcting an output of at least one of the sensor cell and the monitor cell based on an amplitude and a cycle of a pulsation of the output is provided as the electrical correction means.

6. The gas concentration detector according to claim 5, wherein the signal processing means variably sets a correction constant based on the amplitude and the cycle of the pulsation of the output of any one of the sensor cell and the monitor cell.

7. The gas concentration detector according to claim 6, wherein the signal processing means performs smoothing correction on the respective outputs of the sensor cell and the monitor cell by using smoothing constants, respectively determined, based on the amplitudes and the cycles of the pulsations of the outputs of the sensor cell and the monitor cell.

8. The gas concentration detector according to claim 7, further comprising:
a pump cell for exhausting oxygen in the gas to be measured, introduced into the chamber, to an exterior or for introducing oxygen from the exterior so as to adjust the oxygen concentration in the chamber.

9. The gas concentration detector according to claim 1, further comprising:
a pump cell for exhausting oxygen in the gas to be measured, introduced into the chamber, to an exterior or for introducing oxygen from the exterior so as to adjust the oxygen concentration in the chamber.

10. The gas concentration detector according to claim 9, the pump cell further comprising:
a solid electrolyte body having oxygen ion conductivity and a pair of electrodes formed on surfaces of the solid electrolyte body, wherein
the oxygen concentration in the chamber is controlled by controlling a voltage applied to the pair of electrodes in accordance with a current value of a current flowing between the pair of electrodes or in accordance with the output of the monitor cell.

11. The gas concentration detector according to claim 10, wherein the sensor cell further comprising:
a solid electrolyte body having oxygen ion conductivity and a pair of electrodes formed on surfaces of the solid electrolyte body; and
a concentration of the specific gas component and a concentration of remaining oxygen in the chamber are detected based on a current value of a current flowing between the pair of electrodes when a predetermined voltage is applied to the pair of electrodes.

12. The gas concentration detector according to claim 11, wherein the monitor cell further comprises:
   a solid electrolyte body having oxygen ion conductivity;
   a pair of electrodes formed on surfaces of the solid electrolyte body; and
   a concentration of remaining oxygen in the chamber is detected based on a current value of a current flowing between the pair of electrodes or based on electromotive force generated between the pair of electrodes when a predetermined voltage is applied to the pair of electrodes.

13. The gas concentration detector according to claim 1, wherein the concentration of the specific gas component in the gas to be measured is detected based on a difference in output between the sensor cell and the monitor cell.

14. The gas concentration detector according to claim 12, wherein the concentration of the specific gas component in the gas to be measured is detected based on a difference in output between the sensor cell and the monitor cell.

15. The gas concentration detector according to claim 1, wherein the sensor cell and the monitor cell are provided in the chamber so as to be proximate to each other.

16. The gas concentration detector according to claim 14, wherein the sensor cell and the monitor cell are provided in the chamber so as to be proximate to each other.

17. The concentration detector according to claim 1, wherein
   the specific gas component is NOx; and
   electrodes of the sensor cell, provided so as to face the chamber, are made of an electrode material active to reduction of NOx, and electrodes of the monitor cell, provided so as to face the chamber, are made of an electrode material inactive to reduction of NOx.

* * * * *